United States Patent

Smith et al.

[11] 3,981,264
[45] Sept. 21, 1976

[54] DROPLET IMPACT RECORDER

[75] Inventors: Charles A. Smith, Fountain Valley; Arthur D. Warren, Los Angeles, both of Calif.

[73] Assignee: The United States of America as represented by the Secretary of the Air Force, Washington, D.C.

[22] Filed: Jan. 16, 1975

[21] Appl. No.: 541,483

[52] U.S. Cl. .................. 116/114 AM; 23/230 R
[51] Int. Cl.² .................. G01N 33/22; G03C 1/74
[58] Field of Search .............. 116/114 AM, 114 AB, 116/117 R, 114 J, 118 A; 23/230 R, 253 TP; 8/4; 96/99

[56] References Cited
UNITED STATES PATENTS

| | | | |
|---|---|---|---|
| 2,943,594 | 7/1960 | Price | 116/114 AM |
| 3,114,634 | 12/1963 | Brown et al. | 96/99 |
| 3,217,689 | 11/1965 | Knight et al. | 116/114 AM |
| 3,597,263 | 8/1971 | Bancroft et al. | 23/253 TP |
| 3,753,652 | 8/1973 | Gassmann et al. | 23/230 R |
| 3,820,953 | 6/1974 | McEwan et al. | 116/114 AM X |

*Primary Examiner*—Richard C. Queisser
*Assistant Examiner*—Daniel M. Yasich
*Attorney, Agent, or Firm*—Joseph E. Rusz; William J. O'Brien

[57] ABSTRACT

A method for recording the distribution pattern of droplets emanating from a droplet producing source by exposing a dye coated film base to the impact of a droplet fallout. The dye reacts with the chemical component of the droplets to record and retain an exact pattern of the droplets' fallout.

2 Claims, 2 Drawing Figures

# DROPLET IMPACT RECORDER

STATEMENT OF GOVERNMENT INTEREST

The invention described herein may be manufactured and used by or for the Government for governmental purposes without the payment of any royalty thereon.

BACKGROUND OF THE INVENTION

The present invention relates to a means for recording droplet impacts. More particularly, this invention concerns itself with a means for measuring and detecting the production of liquid droplets formed from unreacted rocket motor fuel.

With the recent advent of missile and satellite systems, considerable interest has been generated in the development of testing means for evaluating the operational efficiency of rocket motors. These motors, especially those of the smaller type, are normally operated in space in a pulsed mode; during this operation, a certain amount of fuel and/or oxidizer is expelled without reaction. This phenomenon is most pronounced at the beginning or end of operation of the motor, due to irregularities in the rates of opening of the fuel and oxidizer supply valves and the low temperatures and pressures in the combustion chamber.

The unreacted material which is expelled from a rocket motor is of interest because it indicates imcomplete reaction, it may be highly corrosive, and because it may interfere in various ways with any optical systems used on the space vehicle. These optical systems may have a variety of functions, including scientific observations, spacecraft attitude control, and tracking, guidance, and target discrimination. As the optical systems used on spacecraft become more sensitive and capable of more refined discrimination, the potential interference due to contamination becomes more serious.

In addition to optical systems, engine-produced contaminants can interfere with other important systems on the spacecraft, such as thermal control coatings and solar cells. Finally, certain reaction products deposited on surfaces have the potential of being more explosive than dynamite and are shock sensitive.

For engine diagnosis and testing, it is desirable to be able to observe the quantity and size of particles of unreacted material, and to be able to state at which part of the rocket motor pulse the material was expelled. However, since these materials are normally volatile, collection is very difficult. In addition, any droplets which are formed may be very small. The customary method of visual analysis and evaluation of the droplet characteristics has not proven successful. The effectiveness of such a method depends entirely on the experience, judgment and ability of the individuals conducting the test analysis, and the results obtained vary accordingly and are lacking in sufficient reliability. However, with the present invention, the problems referred to above have been overcome since fairly accurate test results can now be obtained in a reproducible manner not heretofore achieved.

As far as is known, no techniques are presently available which allow measurement of number, size, and time of production of droplets from rocket motors which operate within the space environment.

SUMMARY OF THE INVENTION

The present invention provides a novel droplet impact recorder and a method for accurately analyzing the number, size and pattern of droplets formed during the expulsion of unreacted fuel components from an operating rocket motor. In essence, the invention consists of the use of photographic film, either unaltered or modified, to provide a permanent record of impacts of droplets of unreacted fuel. This record may be formed immediately upon impact of the droplet or upon subsequent treatment of the film.

Black and white photographic film consists of a base, normally a polyester or cellulose acetate, which provides mechanical strength, and an emulsion, normally gelatin, containing very fine particles of silver bromide or silver iodide or other silver halide. A sensitizing dye is usually added to increase the wavelength range to which the film is sensitive.

Droplets which strike the film produced a record of their size and distribution. Certain unreacted rocket fuel components affect the film in two ways. First, the gelatin emulsion dissolves upon evaporation of the fuel component leaving a crater in the emulsion. Secondly, the silver particles are reduced to brown metallic silver by chemical reaction with the unreacted fuel component. This results in a permanent record that can be used in analysis of droplet patterns for rocket motors. It is especially useful in providing experimental data to verify rocket exhaust plume effects on communications and to evaluate the effect of plume contamination on spacecraft surfaces.

Accordingly, the primary object of this invention is to provide a means for reliably and accurately analyzing the droplet pattern formed during the expulsion of unreacted fuel components from an operating rocket motor.

Another object of this invention is to provide a means for providing an accurate analysis of spray patterns from atomizer nozzles on burners, diesel engines, gas turbines and crop spraying equipment.

Still another object of this invention is to provide a means for producing an exact and permanent record of aerosol production from smoke stacks, automobile engine exhausts, chemical processes and processing equipment, crop spraying, paint spraying and similar applications.

The above and still other objects and advantages of the present invention will become more readily apparent upon consideration of the following detailed description thereof when taken in conjunction with the accompanying drawing.

DESCRIPTION OF THE PREFERRED EMBODIMENTS

Figure 1:
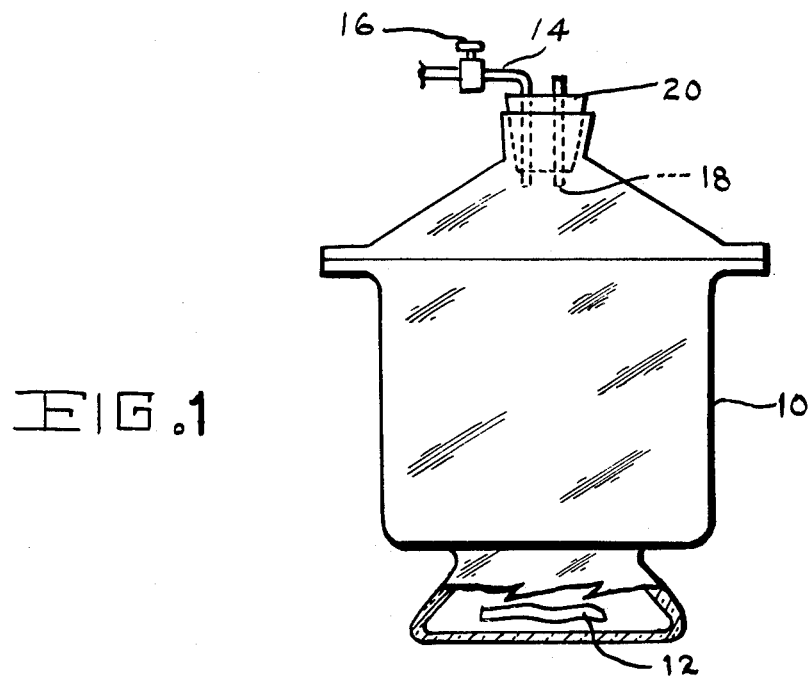
FIG. 1 is a schematic view partly in section illustrating an apparatus for testing the droplet records of this invention.

The foregoing objects are accomplished, in accordance with this invention, through the use of photographic film, either unaltered or modified to provide a permanent record of droplet impacts. This record may be formed immediately upon impact of the droplet or upon subsequent treatment of the film. Generally, photographic film consists of a base, normally polyester or cellulose acetate, which provides mechanical strength, and an emulsion, normally gelatin, containing very fine particles of silver bromide or silver iodide or other silver halide. A sensitizing dye is usually added to increase the wavelength range to which the film is sensitive. The film is placed in an appropriate location adjacent to the rocket motor to be tested. Droplets of unreacted fuel which strike the film produce a record of the droplet pattern in a number of ways. For example, certain chemicals, such as monomethyl hydrazine (MMH), a common rocket fuel, react in two ways with the film emulsion: (a) the gelatin dissolves, and upon evaporation of MMH a crater is formed and (b) the white silver bromide or silver iodide particles are reduced to brown metallic silver by chemical reaction with the MMH. Nitrogen tetroxide, a common rocket fuel oxidizer, evidently vaporizes too rapidly to produce a permanent record on unmodified film, so a different technique is used: the emulsion layer of the film is first removed by soaking in a hot dilute solution of sodium hydroxide in water, leaving only the film base, and this is then washed, dried, and coated with a thin layer of some dye which will undergo a permanent color change when struck by a droplet of nitrogen tetroxide.

Although the use of a black and white photographic film base is preferable, the invention is not limited thereto since any plastic substrate, such as cellulose acetate, polyester, polyethylene, or polypropylene, may be used as the medium for holding the dye. A photographic film base is particularly suitable because, having sprocket holes, it may be pulled through a droplet-filled plume or exhaust allowing a time resolved map of droplet size, distribution and composition to be obtained.

A dye which has been found suitable for use is HE-801 Fat Black HB, produced by the Carbric Color Division of American Hoechst Corp. Droplet impacts of other fuels or oxidizers may also be recorded by the techniques described herein. In addition, droplet impacts of other materials, not as reactive chemically as those described previously, may be recorded through appropriate treatment of the film either before or after exposure to the droplets being recorded in order to enhance the spots produced. Conventional dyes suitable to each type of chemical compound sought are readily available for treating the film. Color film may also be employed since the interaction of the droplets with the dyes incorporated in the film will result in a sensitive method for certain compounds.

Some of the advantages of using photographic film as a basis for recording droplet impacts reside in the fact that very careful quality control is utilized in film manufacture, essentially eliminating batch variations. Also, the silver bromide and silver iodide in the film are extremely sensitive to certain compounds, such as monomethyl hydrazine. In addition, photographic film is available in a wide variety of sizes and with a wide range of emulsion thicknesses, and equipment is available which allows exposure of the film to the droplet source for a precisely known length of time. Image analysis equipment is commercially available to analyze the droplet impact record on film very rapidly and accurately.

The following examples are presented for the purpose of pointing out in detail the practice of the invention. The examples illustrate specific embodiments of the invention and both use Kodak fine grain spectroscopic film, Type 5367, Number 1, in 35 millimeter width having the standard arrangement of sprocket holes. As in many other 35 millimeter films, this consists of a transparent acetate plastic film base, coated on one side with a gelatin emulsion.

EXAMPLE 1

The film was exposed to light but not developed. It was then placed in a 0.05 percent aqueous solution of Malachite Green stain (available from Matheson, Coleman, and Bell, East Rutherford, N.J.) for 2 seconds. Excess solution was immediately removed from the film by blotting with absorbent paper, and it was then dried at room temperature. This technique of film preparation resulted in a high sensitivity to monomethyl hydrazine, which gives a brown crater in the green emulsion layer.

If desired the photographic film may be "cleared", that is, all silver compounds are removed by treatment with sodium thiosulfate ("hypo") until the film is completely transparent, and then washing and drying. Alternatively, any thin transparent plastic material, such as acetate, polyvinyl chloride, or polycarbonate may be coated with a good grade of photographic gelatin, such as is available from Eastman Kodak Company, Rochester, N.Y.

EXAMPLE 2

In this embodiment, the emulsion layer is removed from the acetate film base by immersing it in an aqueous solution of 5 percent by weight of sodium hydroxide for approximately 0.5 hour, and then removing any remaining emulsion by gently rubbing the film base under running water. The film is then rinsed with water and dried. It is then coated on one side with a 0.05 percent solution, by weight, in methyl ethyl ketone, of C.I. Solvent Black 3. A commercial preparation of this dye is HE 801 Fat Black HB, available from American Hoechst Corp., Bridgewater, N.J. This film is highly sensitive to nitrogen tetroxide, which produces a permanent color change to orange with sharply defined edges when it strikes the thin layer of dye on the film. Rather than using the plastic base of photographic film, however, any transparent plastic material may be used, by coating it with dye.

To further illustrate the invention, reference is now made to FIG. 1 of the drawing wherein there is disclosed a testing apparatus for recording droplets of monomethyl hydrazine and nitrogen tetroxide in a vacuum environment. This combination of fuel and oxidizer is normally used in a space vacuum. The apparatus comprises a vacuum desiccator 10. A film 12, prepared in accordance with this invention, is placed in the bottom of the desiccator 10, treated side up. The desiccator 10 is evacuated through conduct means 14 and valve 16 by means of a vacuum pump not shown to a pressure of less than one torr (one millimeter of mercury). A small syringe, not shown, of the type used for certain scientific applications, with a total volume of 10 microliters, is filled with either monomethylhydrazine or nitrogen tetroxide, depending on the film being tested. The syringe needle is then inserted through a rubber septum 18 and rubber stopper 20. Exposure of the contents of the syringe to the lowered pressure in the desiccator resulted in rapid boiling and expelling of small droplets, some of which struck the film. The film was then removed from the desiccator and examined under low power magnification. Characteristic round spots were easily observed and measured, using a measuring eyepiece on the microscope.

Figure 2:
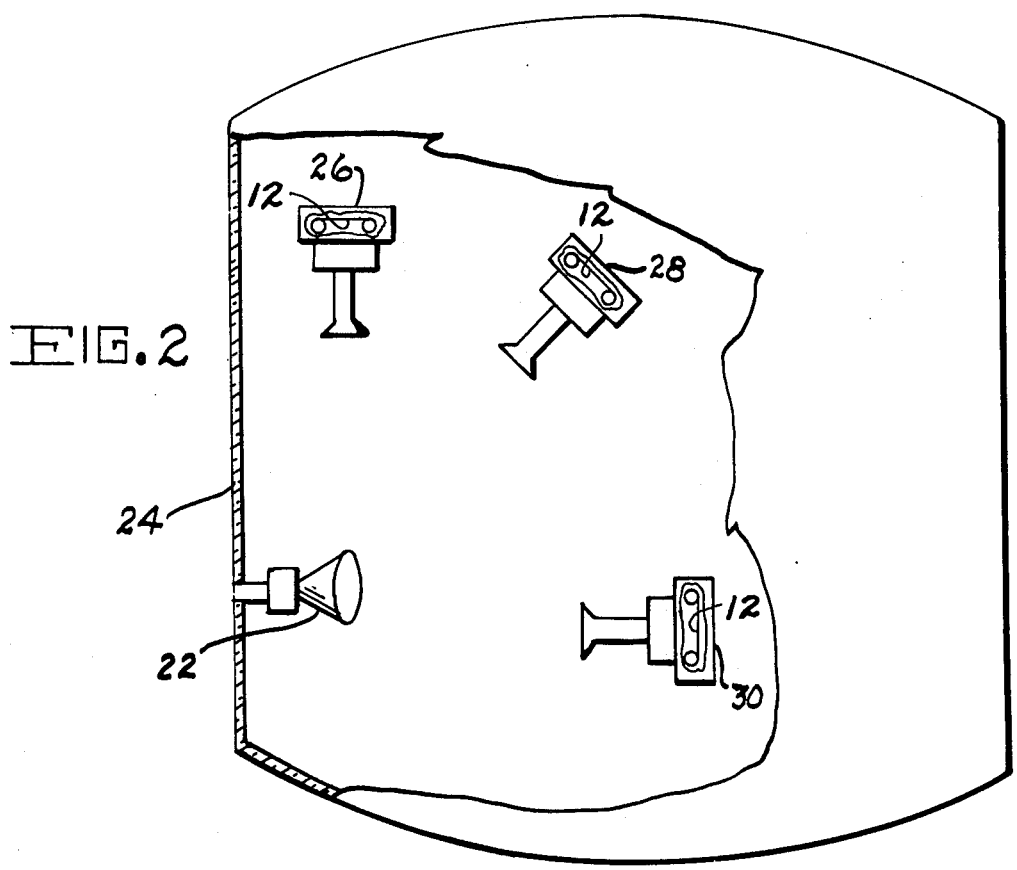
FIG. 2 is a schematic view partly in section illustrating how the droplet recorder of this invention may be positioned relative to a rocket motor.

FIG. 2 of the drawing discloses an arrangement for recording droplets produced by a small rocket motor 22 operating in a vacuum chamber 24. Photographic film 12 prepared in the manner described in Example 1 or 2 is loaded into a series of suitable 35 mm cameras, designated by the numerals 26, 28 and 30, from which the lenses have been removed allowing unreacted fuel component droplets to impinge on the film for recording their size and distribution. These cameras could be either motion picture cameras or still cameras, with provision for remote actuation of the shutter and film advance mechanism, and suitable protection from the fuel, the oxidizer, and the products of their reaction. The cameras containing the prepared film are positioned at predesired distances and angles from the rocket motor, and operated for the desired length of exposure to the unreacted components of the fuel mixture. The unreacted fuel components are propelled from the burning rocket propulsion motor in the form of droplets toward the camera, through the lens opening and onto the surface of the film positioned within the interior of the camera body. Through the manipulation of the film advance mechanism, intermittent portions of the film can be exposed to the droplets for predetermined periods of time if desired by testing personnel. There is no danger of damage to the film or to the modified camera due to heat or gas pressure from the rocket motor, since the motors being tested are small attitude control types. These have quite low thrusts, and are normally operated in a pulsed mode, which would further decrease any possibility of damage.

The invention has been tested, as described above, with monomethylhydrazine as a typical fuel and nitrogen tetroxide as a typical oxidizer. These materials are hypergolic, that is, they react when they contact each other, producing nitrogen, carbon dioxide, and water, all of which are gases at the temperature of reaction.

Although visual examination by low power microscope was utilized to examine the permanent record of droplet distribution, an image analysis system such as that produced by Imanco, Inc. could be utilized to determine the number of particles which had hit the film and classify them by size.

A knowledge of the droplet size, quantity, spatial distribution, and time of expulsion (after start of fuel and oxidizer injection) is useful in analyzing the contamination potential of a rocket motor, and in developing possible changes to lessen contaminant production. Small rocket motors of the type used for attitude control of spacecraft are most efficient when operated at a particular thrust level, rather than attempting to throttle them to other thrusts. However, this requires that they be pulsed, rather than operated steadily. During the start of the pulse and after shutdown, when chamber temperatures and pressures are low, a significant amount of unreacted or partially reacted fuel or oxidizer may be released. These materials may be gas, liquid, or solid. These materials may interfere with spacecraft operation in a number of ways. They may be propelled by the gases from the motor and strike the surfaces of optical instruments. They may change the optical properties of thermal control coatings, resulting in undesired temperature changes. They may be "seen" by an optical instrument on the spacecraft either as an increased ratio of noise to the desired signal or as a discrete object.

Depending on a multitude of factors, particulate contamination may cause effects ranging from completely negligible to those capable of causing failure of the mission.

The invention has been described with reference to specific embodiments thereof. However, it is to be understood that the description of the present invention is made for the purpose of illustration only, and that all the modifications and alterations as are included within the scope of the appended claims are intended to be included herein.

What is claimed is:

1. A method for recording the droplet fallout distribution pattern of an unreacted monomethyl hydrazine fuel component emanating from the exhaust source of a rocket propulsion motor in a closed testing environment which comprises the steps of:
   a. providing a photographic film base in the testing environment having a silver alloy particle containing gelatin coating on at least one surface thereof, said particles having a predetermined sensitivity toward monomethyl hydrazine;
   b. exposing at least a portion of said one surface of said coated photographic film base to the impact of said droplet fallout for a period of time sufficient to record and retain an exact droplet pattern of the said unreacted monomethyl hydrazine fuel component.

2. A method in accordance with claim 1 wherein separate portions of said surface of said film are exposed intermittently for predetermined periods of time.

* * * * *